United States Patent [19]
Okabe et al.

[11] Patent Number: 4,757,144
[45] Date of Patent: Jul. 12, 1988

[54] PREPARING TERTIARY AMINE FROM FORMALDEHYDE AND PRIMARY AND/OR SECONDARY AMINE

[75] Inventors: Kazuhiko Okabe, Wakayama; Yukinaga Yokota, Osaka; Kazuhito Matsutani; Tatuhiro Imanaka, both of Wakayama, all of Japan

[73] Assignee: Kao Corporation, Tokyo, Japan

[21] Appl. No.: 913,621

[22] Filed: Sep. 30, 1986

Related U.S. Application Data

[63] Continuation of Ser. No. 673,248, Nov. 20, 1984, abandoned.

[30] Foreign Application Priority Data

Dec. 16, 1983 [JP] Japan ................... 58-238221

[51] Int. Cl.$^4$ ............ C07C 85/08; C07C 87/127; C07C 87/14; C07C 87/28
[52] U.S. Cl. ................... 544/404; 544/106; 546/184; 548/579; 564/398; 564/446; 564/473
[58] Field of Search ........... 564/398, 446, 473; 544/106, 404; 546/184; 548/579

[56] References Cited

U.S. PATENT DOCUMENTS

| | | | |
|---|---|---|---|
| 2,776,313 | 1/1957 | Lappin et al. | 564/398 |
| 2,809,995 | 10/1957 | Noeske et al. | 564/473 |
| 3,336,386 | 8/1967 | Dovell et al. | 564/398 |
| 3,522,309 | 7/1970 | Kirby | 564/446 |
| 3,597,438 | 8/1971 | Brake | 564/398 |
| 4,210,602 | 7/1980 | Bergfeld et al. | 564/398 |

Primary Examiner—J. E. Evans
Attorney, Agent, or Firm—Flynn, Thiel, Boutell & Tanis

[57] ABSTRACT

A tertiary amine is effectively prepared by reacting a primary or secondary amine with formaldehyde in the presence of a palladium or platinum catalyst at a hydrogen pressure of 3 to 50 kg/cm2 (gauge pressure) at a temperature of 80° to 180° C., by controlling the addition of formaldehyde to the starting amine.

4 Claims, No Drawings

PREPARING TERTIARY AMINE FROM FORMALDEHYDE AND PRIMARY AND/OR SECONDARY AMINE

This application is a continuation of U.S. Ser. No. 673,248, filed Nov. 20, 1984, now abandoned.

The present invention relates to a process for preparing a tertiary amine, and more particularly to a process for preparing a tertiary amine by reacting a primary or secondary amine with formaldehyde in the presence of a palladium or platinum catalyst under hydrogen pressure to effect N-methylation, whereby the corresponding tertiary amine is prepared in high yields.

The tertiary amines produced from various primary and secondary amines by the process of the present invention are useful in various ways, for example, as intermediates for the preparation of emulsifiers, dispersants, rust inhibitors, germicides, dye-assist agents for fibers, softening agents for fiber, etc. and as catalysts for the production of urethane foam, etc.

It is well known that a tertiary amine can be obtained by reacting a long-chain aliphatic primary or secondary amine with formaldehyde and hydrogen in the presence of a hydrogenation catalyst. However, this method has disadvantages in that the yields of the desired tertiary amines are low and undesirable by-products are formed. Japanese Patent Publication No. 17905/1964 and Japanese Patent Laid-Open No. 9019/1980 discloses improved methods thereof. According to the method of Japanese Patent Publication No. 17905/1964, a lower carboxylic acid is added as an additional catalyst to the reaction system in order to inhibit the formation of undesirable by-products. However, the examples of this patent specification revealed that the yield of the desired amine was 88% at best and undesirable by-products were formed in a yield of 10% or higher even when a primary or secondary amine was used as a starting material, Raney nickel was used as a catalyst and a lower carboxylic acid such as acetic acid was added as an additional catalyst. Accordingly, this method has disadvantages in that it requires a large quantity of catalyst, the addition of the additional catalyst is inadequate to inhibit the formation of by-products and the selectivity of the catalyst varies depending on amine species. Furthermore, the addition of foreign matter to the reaction system is inevitable in this method so that the product must be separated and purified after the reaction, that is, this method requires unnecessary stages and hence is not preferred from the viewpoint of operation.

Japanese Patent Laid-Open No. 9019/1980 discloses a method wherein a conventional nickel catalyst for hydrogenation is used and particularly, a nickel catalyst supported on a carrier is effective. However, this method requires an operation for activating the catalyst by contacting it with hydrogen at a temperature of as high as 180° to 230° C. before an N-methylation reaction is carried out by hydrogenation, as exemplified in Examples 4 and 5 where long-chain secondary amines are used as starting materials. Further, from the viewpoint of the characteristics of the catalyst, it is necessary to continuously pass hydrogen through the reaction system and continuously discharge water present in the reaction system, such as water formed by the reaction and derived from formalin to the outside of the process line. Thus, the method disclosed in the Japanese Patent Laid-Open No. 9019/1980 has disadvantages caused by the characteristics of the nickel catalyst supported on a carrier in that it is necessary to carry out an additional operation for previously activating the catalyst with hydrogen at an elevated temperature and water present in the reaction system must be continuously discharged to the outside of the process line, thus complicating the method.

Limitations on the operation and reaction conditions as described in the aforementioned publications also restrict the characteristics of the catalyst which catalyzes the main reaction so that the above methods are manufacturing processes which are restricted as regards the reaction conditions.

We have made studies to eliminate disadvantages associated with conventional methods and to develop a method for obtaining the desired tertiary amine in high yields with high selectivity without limiting the starting material to specific amine species. As a result, we have found a method of preparing the desired tertiary amine in high yields without using any specific additive and cocatalyst and without particular limitation on reaction conditions and starting material species.

In the course of our studies, we have attempted analysis of the reaction mechanism of the main reaction, reaction products and by-products by carrying out the reaction using a conventional hydrogenation catalyst. As a result, we have found that, with a conventional Raney nickel catalyst or a supported nickel catalyst, the selectivity and catalytic activity which greatly affect the hydrogenolysis reaction (hydrogenating dehydration) of the main reaction, mechanism are insufficient, side reactions are liable to take place and the decomposition gas derived from amines and formaldehyde is adsorbed by the catalyst and tends to denature the surface of the catalyst. Particularly when primary amines, lower amines or polyamines are used as starting materials, the above-mentioned phenomena are liable to occur and it is necessary to add additives, carry out an operation for stabilizing the catalyst or limit the reaction conditions in order to control such side reactions. Though these countermeasures can give more or less satisfactory results, they cannot cope with amines which tend to cause side reactions. This is because the nickel catalyst is inferior in hydrogenolysis characteristics (activity and selectivity) which are required of the catalyst for the main reaction so that a large quantity of the catalyst is required, leading to the formation of undesirable by-products. Namely, the above-described troubles are due to the limited selectivity of the catalyst in this reaction.

From the results obtained by using these conventional catalysts, we have concluded that a catalyst exhibiting high activity and high selectivity is indispensable for the main reaction and found that among noble metal elements, palladium and platinum in a very small quantity of 10 to 500 ppm (in terms of catalytic metal) based on that of the amine are effective in respect of hydrogenolysis characteristics required for the main reaction. The present invention is based on this finding.

Accordingly, the present invention provides a process for preparing a tertiary amine by reacting a primary or secondary amine with formaldehyde in the presence of a palladium or platinum catalyst under a hydrogen pressure of 3 to 50 kg/cm$^2$ (gauge pressure) and at a temperature of 80° to 180° C.

The process of the present invention is the one which has for the first time enabled various tertiary amines to be obtained in high yields and in high purities starting with primary amines, secondary amines or polyamines with the use of a small quantity of a palladium or platinum catalyst instead of conventional catalysts which have caused various troubles.

According to the process of the present invention, the intended tertiary amine can be quantitatively obtained from the starting material, and even when primary amines, secondary amines or polyamines which tend to form by-products in the conventional methods are used as the starting materials, the corresponding tertiary amines can be obtained in yields of as high as 95% or above. Further, since catalyst performance is superior, it is not necessary to use any additives or any cocatalysts in order to enhance the selectivity and yield, nor to carry out a particular operation for enhancing the catalyst activity. Furthermore, the reaction can be terminated in a short time even with a very small quantity of the catalyst.

The palladium or platinum catalyst used in the reaction of the present invention has a high activity and its activity per metal unit is at least several tens of times as high as that of a Raney nickel catalyst or a conventional supported nickel catalyst. Hence, the reaction can be carried out by using a catalytic metal in a quantity of from several tens of ppm to several hundreds of ppm based on that of the starting amine. Palladium and platinum used in the present invention are expensive as compared with ordinary metals, but the reaction can be carried out by the use of a very small amount of palladium or platinum as mentioned above and they are excellent in catalytic durability so that the catalyst activity is scarcely reduced even after they are used several times.

The catalyst of the present invention can be regenerated and the performance of the regenerated catalyst is comparable to that of the original one. Since the catalyst is excellent in selectivity, the desired tertiary amines can be obtained in high yields and the resulting amines have a good quality so that the catalyst of the present invention has an advantage in cost as compared with conventional catalysts.

Palladium and platinum which are used as catalysts in the present invention have a unique effect on the hydrogenolysis (dehydration) reaction of N-methylol compounds in the chemical reaction of the present invention, while no remarkable effects can be obtained by the use of other platinum group metals of Group VIII of the Periodic Table, such as rhodium, ruthenium, osmium or iridium and other elements.

The catalyst of the present invention may be in the form of a salt or an oxide of palladium or platinum, preferably supported on a suitable carrier. Any known carrier materials such as carbon, silica, silica-alumina, alumina, diatomaceous earth, natural or synthetic zeolite, etc. can be used. Palladium or platinum (as catalytic metal) may be combined with the carrier in any ratio (for example, 1:99 or 50:50), and preferably the quantity of the catalytic metal to be supported on a carrier is 0.5 to 20% by weight. In the practice of the present invention, palladium and platinum may be used in combination, and a small amount of a third component may be added unless it exhibits an adverse effect on the present invention. The catalyst may be commercially available supported one, or may be the one prepared in the following manner. For example, the catalyst can be supported on a carrier by a method (impregnation method) wherein a carrier material is thoroughly impregnated with a solution of an appropriate palladium or platinum salt and then dried and calcined; a method (precipitation method) wherein a carrier material is added to an aqueous solution of an appropriate palladium or platinum salt, for example, an aqueous solution of palladium or platinum nitrate or sulfate and an aqueous solution of an alkali such as sodium carbonate or sodium hydroxide is added thereto under stirring to precipitate the metal on the carrier; a method wherein the precipitated catalyst is calcined; or a method wherein a reducing treatment is previously carried out with a reducing agent. The obtained palladium or platinum catalyst can be used in the reaction simply by feeding it together with the starting amine into a reactor, introducing hydrogen thereinto and heating the reactants to a required reaction temperature.

Now the outline of the process of the present invention will be described.

A primary or secondary amine which will be described hereinafter is fed into a reactor, a palladium or platinum catalyst is added thereto and hydrogen is introduced into the reactor under stirring. The hydrogen pressure is set at from 3 to 50 kg/cm$^2$, preferably 3 to 20 kg/cm$^2$ (gauge pressure) and the temperature is elevated to from 80° to 180° C., preferably 100° to 150° C. After the temperature has reached the required reaction temperature, formaldehyde is added to the reaction system. Preferably, the addition is continuously carried out over a long period of time.

Formaldehyde which is used in the present invention may be in the form of an aqueous solution thereof, formalin, or a methanol solution, a methanolic formaldehyde solution. The solution is preferred to have a formaldehyde concentration of 30 to 60 percent by weight, preferably 35 to 50 percent by weight. Especially formalin is preferable. Formaldehyde and the starting amine are used in a equimolar quantity. Strictly speaking, an equimolar quantity of formaldehyde for one active hydrogen of the amino group is used. Usually, formaldehyde is used in a quantity of 1.0 to 1.2 equivalents for one active hydrogen of the amino group. The reaction time varies depending on the quantity of the catalyst to be added and the feed rate of formaldehyde, and is usually in the range of 2 to 5 hr. The catalyst is used in a quantity of 10 to 500 ppm (in terms of catalytic metallic palladium or platinum) based on that of the amine. Though a larger quantity of the catalyst may be used, the quantity in the range of 10 to 100 ppm will suffice for the purpose of the present invention and the catalyst has excellent durability so that it can be repeatedly used. Accordingly, the quantity of the catalyst to be used in one operation is further reduced.

The reactor may be a closed system under hydrogen pressure and the presence of the water formed by the reaction, formalin, etc. together with the amine does not affect the catalytic activity. When an excess of formaldehyde is present, small quantities of gases may be continuously discharged under hydrogen pressure to expel excessive formaldehyde or to expel lower gases originating from the starting amine.

After the reaction is completed, the reaction product is distilled as such, or it is distilled after the filtration of the catalyst, or only the catalyst is removed as such by filtration, whereby the desired tertiary amine of good quality can be obtained in very high yields.

For example, the reaction of a long-chain aliphatic secondary amine of the formula $R^1R^2NH$ (wherein $R^1$ and $R^2$ may be the same or different groups and each is a straight-chain or branched saturated or unsaturated hydrocarbon group having 8 to 22 carbon atoms) with formaldehyde was carried out under such conditions that a catalyst composed of 5% palladium on a carbon carrier was used in a quantity of 0.05 wt. % based on that of the amine (25 ppm in terms of metallic palladium based on that of the amine), the reaction temperature was 140° C., hydrogen pressure was 15 kg/cm² (gauge pressure), an equimolar quantity of formalin was added over a period of 4 hr and aging was carried out for 0.5 hr. The reaction products composed of at least 99% of a pure tertiary amine were obtained. Since the catalyst was excellent in selectivity, high-purity, high-quality tertiary amines were obtained merely by removing the used catalyst by filtration after the completion of the reaction. Since the long-chain aliphatic dialkylamines obtained by this reaction have a high boiling point, their purification by distillation is industrially difficult so that they may be preferably purified merely by removing the used catalyst by filtration after the reaction. Hence, it is necessary that they are in a high-purity, high-quality form just after the reaction. The process of the present invention will meet this requirement.

In the reaction of a long-chain aliphatic primary amine of the formula $RNH_2$ (wherein R is a straight-chain or branched saturated or unsaturated hydrocarbon group having 8 to 22 carbon atoms) with formaldehyde, the use of a conventional nickel catalyst for hydrogenation tends to cause side reactions and hence a carboxylic acid or other substance must be added to prevent the side reactions. However, it is difficult to improve the selectivity of the catalyst by this method. As seen from the examples of Japanese Patent Publication No. 17905/1964, the yield of the desired tertiary amine, i.e. long-chain monoalkyldimethylamine is about 88% at best. The product contains as much as about 10% of by-products so that purification by distillation must be carried out to obtain the purpose tertiary amine in a higher purity, thus causing the reduction of the yield.

On the contrary, the reaction of the long-chain aliphatic primary amine of the formula $RNH_2$ with formaldehyde in the presence of the catalyst of the present invention could be carried out under such conditions that a catalyst composed of 5% palladium supported on carbon was used in a quantity of 0.1 wt. % based on that of the amine (50 ppm in terms of metallic palladium based on the quantity of the amine), the reaction temperature was 120° C., the hydrogen pressure was 15 kg/cm² (gauge pressure), formalin was added in a quantity of twice by mol that of the amine (i.e. in an equimolar quantity for one active hydrogen atom of the amino group) over a period of 4 hr and aging was carried for 0.5 hr. The reaction product composed of at least 98% of the pure amine (the desired tertiary amine, i.e. long-chain monoalkyldimethylamine) was obtained. The analysis by gas chromatography showed that scarecely any by-product could be detected according to the present process. Thus, a high-purity, high-quality tertiary amine could be obtained merely by removing the used catalyst by filtration after the completion of the reaction in the process of the present invention.

As described above, a tertiary amine can be obtained with high selectivity even in the reaction of a primary amine which is liable to cause side reactions so that when the catalyst of the present invention is used together with a high-purity primary amine as the starting material, the desired high-quality and high-purity tertiary amine which scarcely contains by-products can be quantitatively obtained without distilling and purifying merely by removing the used catalyst by filtration after the completion of the reaction.

When a primary amine containing large quantities of impurities is used as a starting material, a conventional nickel catalyst tends to denature the surface thereof or to adsorb catalyst poison resulting from the impurities and catalytic activity and selectivity are deteriorated.

On the other hand, when the catalyst of the present invention is used, the catalyst has good resistance to poisoning and good durability so that it is not adversely affected by the impurities, its hydrogenolysis activity is not deteriorated and the primary amine component contained in the starting material can be almost quantitatively converted into the corresponding tertiary amine. Therefore, a high-purity, high-quality tertiary amine can be obtained merely by conducting the distillation for removing the impurities originating from the starting primary amine.

When these reactions are carried out in the presence of a conventional nickel catalyst, the long-chain primary amine tends to cause side reactions as mentioned above and the yield of the desired tertiary amine is reduced. Further, when lower primary amines or polyamines having primary amino groups and/or secondary amino groups, such as diamines or triamines, are used as starting materials, much more side reactions take place and the yields of the corresponding tertiary amines are further reduced.

On the other hand, when the catalyst of the present invention is used, the desired tertiary amine can be produced in high yields even when amines which are liable to cause side reactions are used as starting materials, that is, the desired tertiary amine can be produced in high yields without any particular limitations on the amine species.

Examples of the amines suitable for use as starting materials in the present invention include long-chain aliphatic primary amines of the formula $RNH_2$, such as 2-ethylhexylamine, octylamine, 2-octylamine, decylamine, dodecylamine, tridecylamine, tetradecylamine, pentadecylamine, hexadecylamine, heptadecylamine, octadecylamine, nonadecylamine, eicosylamine, heneicosylamine, docosylamine, oleylamine and mixtures thereof; long-chain aliphatic secondary amines of the formula $R^1R^2NH$, such as dioctylamine, didecylamine, didodecylamine, ditridecylamine, ditetradecylamine, dipentadecylamine, dihexadecylamine, diheptadecylamine, dioctadecylamine, dioleylamine, stearyl/oleylamine, stearyl/hexadecylamine, oleyl/hexadecylamine and dieicosylamine; primary amines of the formula $R^1O(CH_2)_3NH_2$, such as 3-(2-ethylhexyloxy)propylamine, 3-(octyloxy)propylamine, (b 3-(decyloxy)propylamine, 3-(dodecyloxy)propylamine, 3-(tetradecyloxy)propylamine, 3-(hexadecyloxy)propylamine and 3-(octadecyloxy)propylamine; secondary amines of the formula

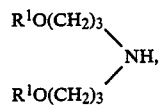

such as di(3(2-ethylhexyloxy)propylamine), di(3-(octyloxy)propyl)amine, di(3-(decyloxy)propyl)amine, di(-dodecyloxy)propylamine, di(3-(tetradecyloxy)propyl)amine, di(3-(hexadecyloxy)propyl)amine and di(3-(octadecyloxy)propyl)amine; polyamines having a primary amino group of the formula $H_2N—(R^3)—NH_2$, such as ethylenediamine, propylenediamine, 1,3-butanediamine, butanediamine, pentamethylenediamine, hexamethylenediamine, heptamethylenediamine and octamethylenediamine; polyamines having primary amino and secondary amino groups of the formula $H_2NR^4(NHR^5)_nNH_2$, such as diethylenetriamine, triethyleneteramine and tetraethylenepentamine; polyamines of the formula $R^1NH[(CH_2)_3NH]_{\overline{n}}H$, such as long-chain monoalkylpropylenediamine and long-chain monoalkyldipropylenetriamine; polyamines of the formula

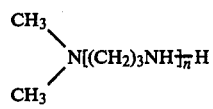

such as N,N-dimethylpropylenediamine and N,N-dimethyldipropylenetriamine; aromatic primary or secondary amines having aromatic groups such as aniline, benzylamine, dibenzylamine and xylenediamine; primary or secondary amines having an alicyclic ring having 4 to 6 carbon atoms, such as cyclobutylamine, cyclopentylamine, cyclohexylamine and dicyclohexylamine; cyclic primary or secondary amines having a heterocyclic ring, such as morpholine, piperidine, piperazine, piperazineethaneamine and pyrrolidine; and primary or secondary amines which are amino alcohols having a monohydric or dihydric hydroxyl group, such as monoethanolamine, isopropanolamine, diethanolamine and diisopropanolamine.

The following examples will further illustrate the present invention.

EXAMPLE 1

500 g of an amine composition of 3.0% of a primary amine, 96.5% of a secondary amine and 0.5% of a long-chain trialkylamine, as a long-chain dialkylamine derived from beef tallow fatty acid as the starting material, and 0.25 g (25 ppm in terms of metallic palladium based on the quantity of the amine) of a catalyst composed of 5% palladium supported on a carbon carrier were fed into a 1-l autoclave and hydrogen was introduced thereinto until hydrogen pressure reached 15 kg/cm² (gauge pressure). The temperature was then kept at 140° C. A 37% aqueous formaldehyde solution in an equimolar quantity to that of the amine was added over a period of 4 hr. After aging for 0.5 hr, the catalyst was removed by filtration. The reaction product consisted of 0.5% or less of unreacted primary and secondary amines and 99.5% or more of a tertiary amine.

COMPARATIVE EXAMPLES 1 AND 2

For the purpose of comparison, the procedure of Example 1 was repeated except that a conventional Raney nickel catalyst and a conventional supported nickel catalyst were used, respectively. The results are shown together with those of Example 1 in Table 1.

TABLE 1

| Catalyst | | Quantity of catalytic metal to be added based on that of amine | Reaction time | Composition of reaction product (%) | |
|---|---|---|---|---|---|
| | | | | unreacted amine | tert. amine |
| Comp. Ex. 1 | Raney nickel | 1% | 4.5 hr | 35.9 | 64.1 |
| Comp. Ex. 2 | supported nickel catalyst | 0.5% | " | 83.7 | 16.3 |
| Example 1 | palladium catalyst | 25 ppm | " | 0.4% | 99.6% |

It is apparent from Table 1 that when the conventional Raney nickel catalyst and the conventional supported nickel catalyst were used as in Comparative Examples 1 and 2, the yields of the desired tertiary amines are considerably low, though larger quantities of the catalysts are added.

Therefore, it becomes necessary to add an additive or to activate the catalyst in order to make an improvement.

On the other hand, the desired tertiary amine could be obtained in a high yield in Example 1 of the present invention, even though the catalytic metal was used in a quantity of as small as 25 ppm based on that of the amine.

EXAMPLE 2

300 g of laurylamine (the analysis by gas chromatography showed that the amine consisted of 99.5% pure amine and 0.5% other ingredients) and 0.3 g (50 ppm in terms of metallic palladium based on the quantity of the amine) of a catalyst composed of 5% palladium supported on a carbon carrier were added to the same reaction vessel as that used in Example 1. Under the conditions of the hydrogen pressure of 15 kg/cm² (gauge pressure) and the temperature of 120° C., a 37% aqueous formaldehyde solution in a quantity of twice by mol that of the amine (in an equimolar quantity for one active hydrogen group of the amino group) was added over a period of 4 hr. After aging for 0.5 hr, the catalyst was removed by filtration. The reaction product consisted of 99.4% of the desired tertiary amine (lauryldimethylamine) and 0.6% of other components.

COMPARATIVE EXAMPLES 3 TO 5

For the purpose of comparison, the procedure of Example 2 was repeated except that a conventional Raney nickel catalyst was used. Since the conversion was very low, additional experiments were conducted wherein acetic acid was added as an additional catalyst. The results are shown together with those of Example 2 in Table 2.

TABLE 2

| | Catalyst | Quantity of catalytic metal to be added based on that of amine | Additive (acetic acid) | Composition of reaction product (%) | | |
|---|---|---|---|---|---|---|
| | | | | lauryldimethylamine | unreacted amine | by-product |
| Comp. Ex. 3 | Raney nickel | 2% | none | 61.9 | 7.5 | 30.6 |
| Comp. | Raney | 2% | 2% | 87.6 | 0.6 | 11.8 |

TABLE 2-continued

| | Catalyst | Quantity of catalytic metal to be added based on that of amine | Additive (acetic acid) | Composition of reaction product (%) | | |
|---|---|---|---|---|---|---|
| | | | | lauryl-dimethyl-amine | unreacted amine | by-product |
| Ex. 4 Comp. Ex. 5 | nickel Raney nickel | 2% | 3% | 85.5 | 2.0 | 12.5 |
| Example 2 | palladium catalyst | 50 ppm | none | 99.4 | 0.1 | 0.5 |

It is apparent from the above results that when the conventional catalyst is used together with the primary amine as a starting material, side reactions are apt to occur so that it is necessary to add a carboxylic acid in order to prevent the side reactions. However, a quantity of the additive exceeding a specified level gives no increased benefits and there is a limit on the yield of the tertiary amine.

On the other hand, the catalyst of the present invention has high activity and selectivity so that the desired tertiary amine (lauryldimethylamine) can be obtained at a high selectivity of at least 99% with 0.5% of by-products by the use of the catalyst of as little as 50 ppm in terms of catalytic metal based on that of the amine.

EXAMPLE 3

The procedure of Example 2 was repeated except that platinum was used as the catalytic metal.

REFERENCE EXAMPLES 1 AND 2

The procedure of Example 2 was repeated except the use of rhodium and ruthenium which were recognized as being capable of serving as hydrogenation catalysts and elements also belonging to Group VIII (platinum group metals) of the Periodic Table. The results of Referential Examples 1 and 2 are shown in Table 3 in comparison with those of Examples 2 and 3.

TABLE 3

| | * catalytic metal | Quantity to be added based on that of amine | Composition of reaction product (%) | | |
|---|---|---|---|---|---|
| | | | lauryl-dimethyl-amine | un-reacted amine | other |
| Ex. 2 | palladium | 50 ppm | 99.4 | 0.1 | 0.5 |

TABLE 3-continued

| | * catalytic metal | Quantity to be added based on that of amine | Composition of reaction product (%) | | |
|---|---|---|---|---|---|
| | | | lauryl-dimethyl-amine | un-reacted amine | other |
| Ex. 3 | platinum | " | 99.1 | 0.2 | 0.7 |
| Referential Ex. 1 | rhodium | " | 11.0 | 44.5 | 44.5 |
| Referential Ex. 2 | ruthenium | " | 9.6 | 37.2 | 53.2 |

*5% metal supported on a carbon carrier.

It is apparent from the above results that palladium and platinum have a unique effect on the reaction of the present invention among the elements which are recognized as being capable of serving as hydrogenation catalysts and belong to the platinum group metals of Group III of the Periodic Table.

EXAMPLES 4 TO 9

200 g of each of hexamethylenediamine, N,N-dimethylpropanediamine, cyclohexylamine, piperazineethaneamine and diethanolamine as starting materials (monoamine and polyamine) and each of palladium and platinum catalysts supported on a carbon carrier in a quantity given in Table 4 were fed into the same reaction vessel as that used in Example 1. Under the conditions of the hydrogen pressure of 15 kg/cm² (gauge pressure) and the reaction temperature of 120° C., an aqueous formaldehyde solution was added over a period of 4 hr. After aging for 0.5 hr, the catalyst was removed by filtration, and the reaction products were analyzed by general analytical methods (e.g. amine value and gas chromatography).

TABLE 4

| | Starting amine | *Quantity of catalytic metal to be added based on that of amine | Molar ratio of formaldehyde to amine | Desired tert. amine | Desired tert. amine GC% | Other GC% |
|---|---|---|---|---|---|---|
| Ex. 4 | hexamethylenediamine | 100 ppm | 4.4 | 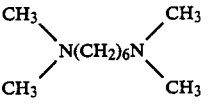 | 96.5 | 3.5 |
| Ex. 5 | N,N—dimethylpropanediamine | 50 ppm | 2.2 | 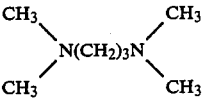 | 96.8 | 3.0 |

TABLE 4-continued

| Starting amine | | *Quantity of catalytic metal to be added based on that of amine | Molar ratio of formaldehyde to amine | Desired tert. amine | Desired tert. amine GC% | Other GC% |
|---|---|---|---|---|---|---|
| Ex. 6 | cyclohexylamine | 50 ppm | 1.1 | cyclohexyl-N(CH$_3$)$_2$ | 98.7 | 1.3 |
| Ex. 7 | piperazineethaneamine | 100 ppm | 3.3 | CH$_3$N(piperazine)NCH$_2$CH$_2$N(CH$_3$)$_2$ | 97.1 | 2.9 |
| Ex. 8 | diethanolamine | 25 ppm | 1.1 | CH$_3$N(CH$_2$CH$_2$OH)$_2$ | 96.0 | 4.0 |
| Ex. 9 | hexmethylenediamine (Pt) | 100 ppm | 4.4 | (CH$_3$)$_2$N(CH$_2$)$_6$N(CH$_3$)$_2$ | 95.1 | 4.9 |

*Examples 4 to 8: palladium catalyst
Example 9: platinum catalyst

COMPARATIVE EXAMPLES 4' TO 8'

Experiments corresponding to Examples 4 to 8 were conducted under the same reaction conditions as those of Examples 4 to 8 by using a conventional Raney nickel catalyst (in a quantity of 2% in terms of catalytic metal based on that of amine). The results are shown in Table 5.

TABLE 5

| | | Comp. Ex. | | | | |
|---|---|---|---|---|---|---|
| | | 4' | 5' | 6' | 7' | 8' |
| Composition GC % | desired tert. amine | 38.6 | 58.1 | 59.2 | 48.6 | 62.4 |
| | by-product | 61.4 | 41.9 | 40.8 | 51.4 | 37.6 |

*The quantities of formaldehyde to be added were the same as those of Examples 4 to 8.
*No additive was used before, during and after the reaction.

It is apparent from the results of Examples 4 to 8 and Comparative Examples 4' to 8' that when monoamines having a primary or secondary amino group, polyamines having primary amino and secondary amino groups, cyclic amines and amino alcohols are used as starting materials in the presence of a conventional Raney nickel catalyst, side reactions take place so that it is difficult to obtain the desired tertiary amines in high yields.

On the other hand, the catalysts of the present invention are excellent in selectivity as seen, from the results of Examples 4 to 8 and give the desired tertiary amines in high yields without any particular limitations on the starting amine species.

EXAMPLES 10 TO 12

Catalysts supported on various carriers were examined in the same process as conducted in Example 2. The catalysts used here were prepared by the precipitation method so as to have 10 percent by weight of the metal thereon. Results are shown in Table 6. It is understood from the results that the process of the invention was effected advantageously with a catalyst supported on a carrier

TABLE 6

| example No. | carrier | metal of catalyst | amount of catalyst metal per amine (PPM) | composition of the reaction product lauryl dimethyl-amine | others |
|---|---|---|---|---|---|
| example 10 | silica-alumina | Pd | 50 | 99.5 | 0.5 |
| example 11 | diatomaceous earth | Pd | 50 | 99.6 | 0.4 |
| example 12 | zeolite | Pd | 50 | 99.4 | 0.6 |

The embodiments of the invention in which an exclusive property or privilege is claimed are defined as follows:

1. A process for preparing an N-methylated tertiary amine, which consists essentially of continuously adding an aqueous or methanolic solution of formaldehyde, for a time period of from 2 to 5 hours, to a reaction mixture consisting of (1) a primary amine, a secondary amine or mixture thereof and (2) from 10 to 500 ppm of palladium or platinum catalyst, calculated as the metal, based on said amine, the reaction mixture being continuously maintained under a hydrogen pressure of from 3 to 50 kg/cm$^2$ gauge and at a temperature of from 80° to 180° C., the total amount of formaldehyde added to said reaction mixture during said time period being from 1.0 to 1.2 equivalents per each active hydrogen of said amine and the accumulation of a stoichiometrically excessive amount of formaldehyde being prevented, whereby to convert substantially quantitatively said primary or secondary amine to the corresponding N-methylated tertiary amine, then removing said catalyst by filtration and recovering said N-methylated tertiary amine.

2. A process as claimed in claim 1, in which said catalyst is supported on a carrier.

3. A process as claimed in claim 1, wherein the formaldehyde solution has a formaldehyde concentration of from 30-60% by wt.

4. A process as claimed in claim 1, wherein the palladium or platinum metal component of the catalyst is in the form of a salt or an oxide.

* * * * *